(12) United States Patent
Palasis et al.

(10) Patent No.: US 6,969,371 B2
(45) Date of Patent: Nov. 29, 2005

(54) LATERAL NEEDLE INJECTION APPARATUS AND METHOD

(75) Inventors: Maria Palasis, Wellesley, MA (US); Arthur Rosenthal, Boston, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 197 days.

(21) Appl. No.: 09/982,934

(22) Filed: Oct. 22, 2001

(65) Prior Publication Data

US 2002/0026150 A1 Feb. 28, 2002

Related U.S. Application Data

(63) Continuation of application No. 09/457,254, filed on Dec. 8, 1999, now Pat. No. 6,319,230.
(60) Provisional application No. 60/133,122, filed on May 7, 1999.

(51) Int. Cl.[7] ............................................. A61M 5/178
(52) U.S. Cl. ................................................ 604/164.01
(58) Field of Search ................................ 604/158, 162, 604/164.01, 164.02, 164.06, 164.08, 164.09, 164.11, 165.01, 165.02, 170.02, 170.03, 171, 173, 264, 372, 523; 606/167, 184, 185

(56) References Cited

U.S. PATENT DOCUMENTS

| | | | |
|---|---|---|---|
| 4,578,061 A | * | 3/1986 | Lemelson ............... 604/170.01 |
| 4,596,556 A | | 6/1986 | Morrow et al. ............... 604/70 |
| 4,790,824 A | | 12/1988 | Morrow et al. ............. 604/143 |
| 5,064,413 A | | 11/1991 | McKinnon et al. ........... 604/70 |
| 5,098,389 A | | 3/1992 | Cappucci .................... 604/158 |
| 5,236,424 A | | 8/1993 | Imran ......................... 604/280 |
| 5,262,128 A | | 11/1993 | Leighton et al. ............. 422/100 |
| 5,324,276 A | | 6/1994 | Rosenberg .................. 604/269 |

(Continued)

FOREIGN PATENT DOCUMENTS

| | | |
|---|---|---|
| CA | 2241615 | 12/1998 |
| DE | 196 07 922 A1 | 9/1997 |
| EP | 0 934 728 A2 | 8/1999 |
| WO | WO 92/10142 A1 | 6/1992 |
| WO | WO 92/10142 * | 6/1992 |
| WO | WO 98/05307 A1 | 2/1998 |
| WO | WO 99/04851 | 2/1999 |
| WO | WO 99/39624 A1 | 8/1999 |
| WO | WO 99/44524 | 9/1999 |
| WO | WO 99/48545 A1 | 9/1999 |
| WO | WO 99/49926 | 10/1999 |

OTHER PUBLICATIONS

Internet Article, 'Taking the "Ouch" Out of Needles: Arrays of Micron–Scale "Microneedles" Offer New Technique For Drug Delivery', John Toon, Released Jun. 22, 1998, 4 pgs.

*Primary Examiner*—LoAn H. Thanh
(74) *Attorney, Agent, or Firm*—Kenyon & Kenyon

(57) ABSTRACT

A device and method for delivering and injecting fluid into heart tissue utilizing a laterally directed needle to increase injectate (fluid) retention in the heart tissue. The device may comprise a catheter having a shaft wherein the distal end of the shaft includes a primary penetrating member and a secondary penetrating member. The secondary penetrating member includes an injection lumen in fluid communication with a pressurized fluid source. The primary penetrating member penetrates the heart tissue at the injection site in a first direction, and the secondary penetrating member penetrates the heart tissue in a second direction different from the first direction such that fluid leakage from the injection site is reduced and the volume of treated tissue is increased.

12 Claims, 4 Drawing Sheets

U.S. PATENT DOCUMENTS

| | | | |
|---|---|---|---|
| 5,354,279 A | 10/1994 | Hofling | 604/164 |
| 5,383,851 A | 1/1995 | McKinnon, Jr. et al. | 604/68 |
| 5,399,163 A | 3/1995 | Peterson et al. | 604/68 |
| 5,403,311 A * | 4/1995 | Abele et al. | 606/49 |
| 5,419,777 A * | 5/1995 | Hofling | 604/264 |
| 5,457,041 A | 10/1995 | Ginaven et al. | 435/172.1 |
| 5,464,395 A * | 11/1995 | Faxon et al. | 604/103.02 |
| 5,472,441 A * | 12/1995 | Edwards et al. | 606/41 |
| 5,478,328 A * | 12/1995 | Silverman et al. | 604/272 |
| 5,520,639 A | 5/1996 | Peterson et al. | 604/68 |
| 5,538,504 A | 7/1996 | Linden et al. | 604/53 |
| 5,672,174 A | 9/1997 | Gough et al. | 606/41 |
| 5,693,029 A * | 12/1997 | Leonhardt | 604/264 |
| 5,697,901 A | 12/1997 | Eriksson | 604/46 |
| 5,702,384 A | 12/1997 | Umeyama et al. | 604/892.1 |
| 5,728,143 A * | 3/1998 | Gough et al. | 607/101 |
| 5,766,164 A | 6/1998 | Mueller et al. | 606/15 |
| 5,782,823 A | 7/1998 | Mueller | 606/7 |
| 5,807,395 A | 9/1998 | Mulier et al. | 606/41 |
| 5,830,222 A | 11/1998 | Makower | 606/159 |
| 5,840,061 A | 11/1998 | Menne et al. | 604/68 |
| 5,843,017 A | 12/1998 | Yoon | 604/22 |
| 5,882,332 A | 3/1999 | Wijay | 604/53 |
| 5,997,525 A | 12/1999 | March et al. | 604/508 |
| 6,063,082 A | 5/2000 | DeVore et al. | 606/45 |
| 6,093,185 A | 7/2000 | Ellis et al. | 606/28 |
| 6,203,556 B1 | 3/2001 | Evans et al. | 606/185 |
| 6,319,230 B1 * | 11/2001 | Palasis et al. | 604/164.01 |

* cited by examiner

LATERAL NEEDLE INJECTION APPARATUS AND METHOD

RELATED APPLICATIONS

This application is a continuation application of application Ser. No. 09/457,254 filed Dec. 8, 1999 now U.S. Pat. No. 6,319,230, which claims the benefit of provisional application Ser. No. 60/133,122, filed May 7, 1999, the entire disclosures of which are incorporated by reference.

This application claims the benefit of Provisional Patent Application Ser. No. 60/133,122, filed May 7, 1999, entitled INCREASED EFFICIENCY DIRECT INJECTION OF THERAPEUTIC AGENTS, which is hereby incorporated by reference.

This application is related to co-pending patent application Ser. No. 09/457,453, filed on even date herewith, entitled INJECTION ARRAY APPARATUS AND METHOD; co-pending patent application Ser. No. 09/457,193, filed on even date herewith, entitled LATERAL NEEDLE-LESS INJECTION APPARATUS AND METHOD; and co-pending patent application Ser. No. 09/456,456, filed on even date herewith, entitled NEEDLE-LESS INJECTION APPARATUS AND METHOD.

FIELD OF THE INVENTION

The present invention generally relates to delivering and injecting fluid into heart tissue. More specifically, the present invention relates to delivering and injecting fluid into heart tissue utilizing a laterally directed needle.

BACKGROUND OF THE INVENTION

Injection catheters may be used to inject therapeutic or diagnostic agents into a variety of organs, such as the heart. In the case of injecting a therapeutic agent into the heart, 27 or 28 gauge needles are generally used to inject solutions carrying genes, proteins, or drugs directly into the myocardium. A typical volume of an agent delivered to an injection site is about 100 microliters. A limitation to this method of delivering therapeutic agents to the heart is that the injected fluid tends to leak and/or disperse from the site of the injection after the needle is disengaged from the heart. In fact, fluid may continue to leak over several seconds. In the case of dynamic organs such as the heart, there may be more pronounced leakage with each muscle contraction.

Therapeutic and diagnostic agents may be delivered to a portion of the heart as part of a percutaneous myocardial revascularization (PMR) procedure. PMR is a procedure which is aimed at assuring that the heart is properly oxygenated. Assuring that the heart muscle is adequately supplied with oxygen is critical to sustaining the life of a patient. To receive an adequate supply of oxygen, the heart muscle must be well perfused with blood. In a healthy heart, blood perfusion is accomplished with a system of blood vessels and capillaries. However, it is common for the blood vessels to become occluded (blocked) or stenotic (narrowed). A stenosis may be formed by an atheroma which is typically a harder, calcified substance which forms on the walls of a blood vessel.

Historically, individual stenotic lesions have been treated with a number of medical procedures including coronary bypass surgery, angioplasty, and atherectomy. Coronary bypass surgery typically involves utilizing vascular tissue from another part of the patient's body to construct a shunt around the obstructed vessel. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guide wire and a balloon catheter. In these procedures, a balloon catheter is advanced over a guide wire such that the balloon is positioned proximate a restriction in a diseased vessel. The balloon is then inflated and the restriction in the vessel is opened. A third technique which may be used to treat a stenotic lesion is atherectomy. During an atherectomy procedure, the stenotic lesion is mechanically cut or abraded away from the blood vessel wall.

Coronary by-pass, angioplasty, and atherectomy procedures have all been found effective in treating individual stenotic lesions in relatively large blood vessels. However, the heart muscle is perfused with blood through a network of small vessels and capillaries. In some cases, a large number of stenotic lesions may occur in a large number of locations throughout this network of small blood vessels and capillaries. The torturous path and small diameter of these blood vessels limit access to the stenotic lesions. The sheer number and small size of these stenotic lesions make techniques such as cardiovascular by-pass surgery, angioplasty, and atherectomy impractical.

When techniques which treat individual lesions are not practical, percutaneous myocardial revascularization (PMR) may be used to improve the oxygenation of the myocardial tissue. A PMR procedure generally involves the creation of holes, craters or channels directly into the myocardium of the heart. In a typical laser PMR procedure, these holes are created using radio frequency energy delivered by a catheter having one or more electrodes near its distal end. After the wound has been created, therapeutic agents are sometimes ejected into the heart chamber from the distal end of a catheter.

Positive clinical results have been demonstrated in human patients receiving PMR treatments. These results are believed to be caused in part by blood flowing within the heart chamber through channels in myocardial tissue formed by PMR. Increased blood flow to the myocardium is also believed to be caused in part by the healing response to wound formation. Specifically, the formation of new blood vessels is believed to occur in response to the newly created wound. This response is sometimes referred to as angiogenesis. After the wound has been created, therapeutic agents which are intended to promote angiogenesis are sometimes injected into the heart chamber. A limitation of this procedure is that the therapeutic agent may be quickly carried away by the flow of blood through the heart.

In addition to promoting increased blood flow, it is also believed that PMR improves a patient's condition through denervation. Denervation is the elimination of nerves. The creation of wounds during a PMR procedure results in the elimination of nerve endings which were previously sending pain signals to the brain as a result of hibernating tissue.

Currently available injection catheters are not particularly suitable for accurately delivering small volumes of therapeutic agents to heart tissue. Improved devices and methods are desired to address the problems associated with retention of the agent in the heart tissue as discussed above. This is particularly true for agents carrying genes, proteins, or other angiogenic drugs which may be very expensive, even in small doses.

SUMMARY OF THE INVENTION

The present invention provides an improved apparatus and method for delivering and injecting fluid into heart tissue. The present invention addresses the problems associated with retention of the fluid in the heart tissue by utilizing a laterally directed needle. The present invention may be used to deliver genes, proteins, or drugs directly into the myocardium for purposes of myocardial revascularization.

In an exemplary embodiment, the present invention provides a catheter having a shaft, wherein the distal end of the shaft includes a primary penetrating member and a secondary penetrating member. The primary penetrating member penetrates the heart tissue at the injection site in a first direction, and the secondary penetrating member penetrates the heart tissue in a second direction different from the first direction. The secondary penetrating member includes an injection lumen for delivering a fluid to the heart tissue. By penetrating the tissue in a different direction, fluid leakage from the injection site is reduced.

A plurality of secondary penetrating members, such as microneedles, may be utilized. Any practical number of secondary penetrating members may be used, but preferably 1 to 20 secondary penetrating members are utilized. The secondary penetrating members may have a diameter in the range of approximately 27 to 40 Gauge, and a penetrating length in the range of approximately 0.5 to 5 mm. The primary penetrating member is typically larger than the secondary penetrating members with a diameter in the range of approximately 20 to 36 Gauge, and a penetrating length in the range of approximately 1 to 10 mm.

As mentioned above, the primary penetrating member penetrates the heart tissue at the injection site in a different direction than the secondary penetrating member such that fluid leakage from the injection site is reduced. The primary penetrating member may penetrate the heart tissue generally orthogonal to the tissue surface at the injection site. The secondary penetrating member may penetrate the heart tissue in a direction that is generally lateral to the direction of the primary penetrating member. Preferably, the secondary penetrating member penetrates the heart tissue in a direction that is at an angle of about 5 to about 90 degrees relative to the direction of the primary penetrating member.

The catheter may include a sheath disposed about the shaft. The distal end of the sheath may include a suction head for stabilizing the distal end of the catheter upon the application of suction to the sheath.

The present invention also provides a method of delivering a fluid to heart tissue including the steps of: navigating a catheter substantially as described above in a patient's body until the distal end of the catheter is positioned adjacent the injection site; actuating the primary penetrating member such that the primary penetrating member penetrates the heart tissue in a first direction; actuating the secondary penetrating member such that the secondary penetrating member penetrates the heart tissue in a second direction different from the first direction; and injecting the fluid into the heart tissue via the secondary penetrating member.

Less than approximately 100 microliters of fluid is injected into the heart tissue via the secondary penetrating member. If a plurality of secondary members such as microneedles are used, approximately 1 to 20 microliters of fluid may injected into the heart tissue via each needle. Due to the different penetration direction of the needles, a substantial amount if not all of the fluid is retained in the heart tissue.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1A:
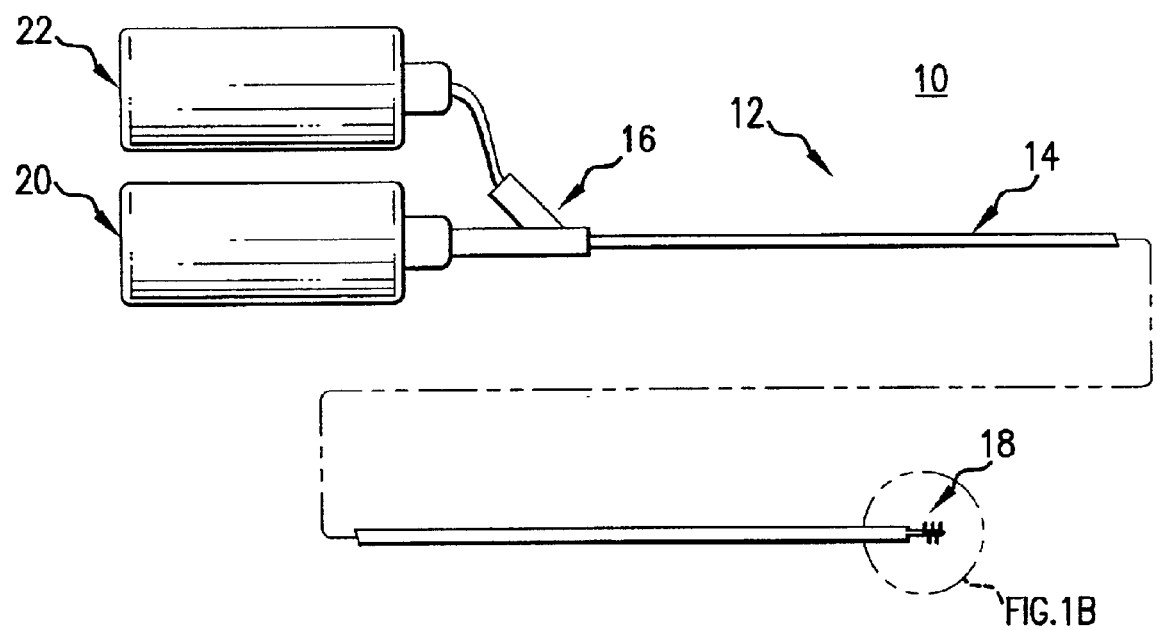
FIG. 1A is a plan view of a catheter system in accordance with an exemplary embodiment of the present invention.

Refer now to FIG. 1A which illustrates a plan view of a catheter system 10 in accordance with an exemplary embodiment of the present invention. Catheter system 10 includes a catheter 12 having an elongate shaft 14. A manifold 16 is connected to the proximal end of the elongate shaft 14. The elongate shaft 14 includes a distal portion 18 which is illustrated in greater detail in FIG. 1B.

A pressurized fluid source 20 is connected to the catheter 12 by way of the manifold 16. Optionally, a vacuum source may be coupled to the side arm of the manifold 16. The pressurized fluid source 20 may comprise a conventional syringe or an automated pressure source such as a high pressure injection system. An example of a high pressure injection system is disclosed in U.S. Pat. No. 5,520,639 to Peterson et al. which is hereby incorporated by reference. Similarly, vacuum source 22 may comprise a conventional syringe or other suitable vacuum means such as a vacuum bottle.

Figure 1B:
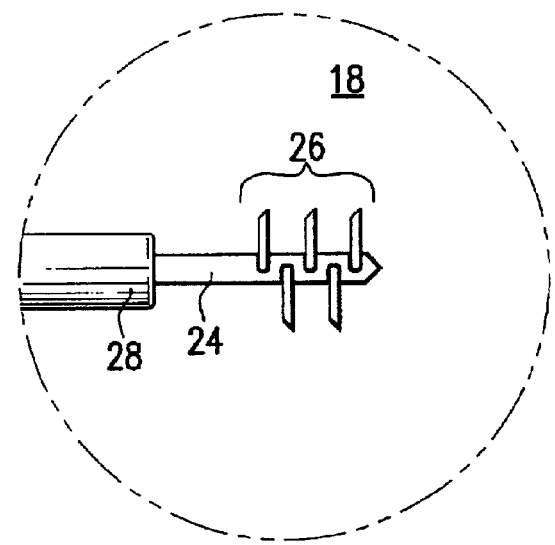
FIG. 1B is an enlarged detailed view of the distal end of the catheter illustrated in FIG. 1A.

Refer now to FIG. 1B which illustrates an enlarged detailed view of the distal portion 18 of the elongate shaft 14. The distal portion 18 of the elongate shaft 14 includes a primary penetrating member 24 coaxially disposed in an elongate outer sheath 28. The primary penetrating member 24 contains a plurality of secondary penetrating members 26 disposed adjacent the distal end thereof. The secondary penetrating members 26 are retractable within the primary penetrating member 24, but are shown in the extended position for purposes of illustration. The proximal end of the secondary penetrating members 26 or a tubular member attached thereto is disposed adjacent the proximal end of the shaft 14 and is in fluid communication with the pressurized fluid source 20 via manifold 16.

Figure 2:
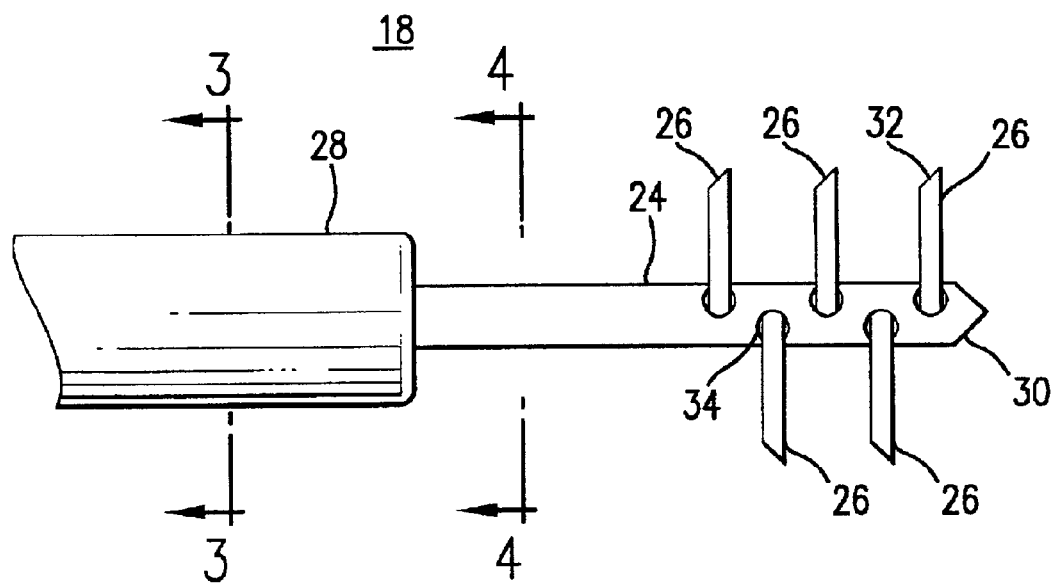
FIG. 2 is a further enlarged view of the distal end of the catheter illustrated in FIG. 1A.

With reference to FIG. 2, the primary penetrating member 24 includes a sharpened distal end 30 to facilitate easy penetration of tissue. Similarly, the distal end 32 of each of the secondary penetrating members 26 are sharpened to facilitate easy penetration of tissue. The secondary penetrating members 26 extend through apertures 34 defined through the wall of the primary penetrating member 24. The apertures 34 each have an axis that is at an angle with the longitudinal axis of the primary penetrating member 24. The axis of each aperture 34 is may be orthogonal to the axis of the primary penetrating member 24 or any other desired angle. The angle of the axis of each aperture 34 determines in part the penetration angle of the secondary members 26 which may vary as discussed in greater detail with reference to FIGS. 6A–6C.

Figure 3:
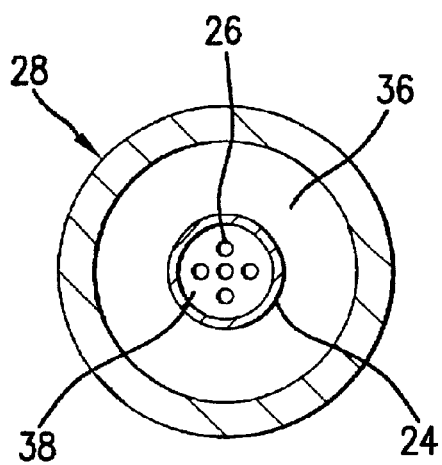
FIG. 3 is a lateral cross-sectional view taken along line 3—3 in FIG. 2.

With reference to FIG. 3, a lateral cross-sectional view taken along line 3—3 in FIG. 2 is shown. The shaft 14 includes an annular lumen 36 defined between the interior of the sheath 28 and the exterior of the primary member 24. The annular lumen 36 may be used to infuse fluids for purposes of fluoroscopic visualization and/or aspiration. Alternatively, the annular lumen 36 may be used to facilitate the application of suction for stabilization purposes as will be discussed in greater detail with reference to FIGS. 7A–7C.

The elongate shaft 14 has characteristics (length, profile, flexibility, pushability, trackability, etc.) suitable for navigation from a remote access site to the treatment site within the human body. For example, the elongate shaft 14 may have characteristics suitable for intravascular navigation to the coronary tissue from a remote access site in the femoral artery. Alternatively, the elongate shaft 14 may have characteristics suitable for transthoracic navigation to the coronary tissue from a remote access point in the upper thorax. Those skilled in the art will recognize that the shaft 14 may have a wide variety of dimensions, materials, constructions, etc. depending on the particular anatomy being traversed.

Figure 4:
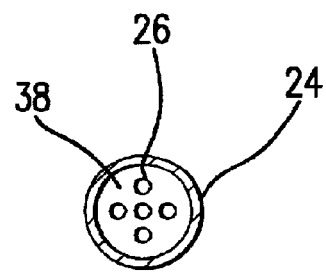
FIG. 4 is a lateral cross-sectional view taken along line 4—4 in FIG. 2.

Refer now to FIG. 4 which illustrates a lateral cross-sectional view taken along line 4—4 in FIG. 2. Primary penetrating member 24 includes an internal lumen 38 containing one or more secondary penetrating members 26. Each secondary penetrating member also includes an injection lumen defined therein. The injection lumens defined in each of the secondary penetrating members 26 are in fluid communication with the pressurized fluid source 20 such that fluid may be readily delivered from the pressurized fluid source through the shaft 14 and into the heart tissue being treated. Fluid communication between the pressurized fluid source 20 and the injection lumens may be defined by a direct connection between the proximal ends of the secondary penetrating members 26 to the source 20 via manifold 16. Such fluid communication may also be defined in part by an intermediate tube connected to the proximal ends of the secondary penetrating members 26 or by the inner lumen 38 of the primary penetrating member 24.

The secondary penetrating members 26 may be fully contained within the inner lumen 38 of the primary penetrating member 24 in the retracted position. In the extended position, the secondary penetrating members 26 extend through apertures 34 defined in the wall of the primary penetrating member 24. To laterally actuate the secondary penetrating members 26 from the retracted position to the extended position, they may be displaced longitudinally and guided through the apertures 34, as will be discussed in greater detail with reference to FIG. 5. Lateral actuation may also be accomplished by other suitable means. Examples of suitable mechanisms for actuating the secondary penetrating members 26 are disclosed in U.S. Pat. No. 4,578,061 to Lemelson, U.S. Pat. No. 5,538,504 to Linden et al., and International Patent Publication No. WO 92/10142 to Makower, the entire disclosures of which are hereby incorporated by reference.

Because the secondary penetrating members 26 must be translated between a generally longitudinal retracted position to a generally lateral extended position, it is preferable that the secondary penetrating members 26 be made of a material capable of sustaining high degrees of strain. Suitable materials include superelastic metals such as nickel titanium alloys and highly elastic polymers such as polyamide and LCP. The secondary penetrating members 26 may have an extended or penetrating length of approximately 0.5 to 5 mm and a diameter of approximately 27 to 40 Gauge. Alternatively, the secondary penetrating members 26 may comprise microneedles as described in co-pending patent application Ser. No. 09/457,453, filed on even date herewith, entitled INJECTION ARRAY APPARATUS AND METHOD, and as described in U.S. Pat. No. 5,697,901 to Eriksson, which are hereby incorporated by reference.

The primary penetrating member 24 may have a length slightly greater than the length of the outer sheath 28, with a penetrating length of approximately 1 to 10 mm. The inside diameter of the primary penetrating member 24 should be sufficiently large to accommodate the desired number of secondary penetrating members 26. Assuming a plurality of secondary penetrating members 26 having the dimensions described above are utilized, the primary penetrating member 24 may have an inside diameter in the range of less than about 20 Gauge and an outside diameter in the range of 20 to 30 Gauge. The primary penetrating member 24 may be formed of stainless steel or other suitable material such as nickel titanium alloy.

To facilitate translation from the generally longitudinal position in the inner lumen 28 of the primary penetrating member 24 to the extended position, a means for directing the secondary penetrating member 26 may be disposed in the distal end of the primary penetrating member 24. The directing means may comprise any of the mechanisms disclosed in Lemelson '061, Linden '504 or Makower '142. The means for directing the secondary penetrating member 26 may alternatively comprise an insert 40 as shown in FIG. 5.

The insert 40 includes a lumen which may be a groove, channel, or slot 42 extending in the longitudinal direction and transitioning to a generally lateral direction adjacent the aperture 34. By displacing the secondary penetrating members 26 relative to the primary penetrating member 24 and the insert 40 disposed therein, the secondary penetrating members 26 are guided from lumen 38, through apertures 34 and into the heart tissue. Displacement of the secondary penetrating members 26 may be accomplished by manual operation at the proximal end of the shaft 14. The proximal end of the secondary penetrating members 26 or a tubular member attached thereto may be manipulated as described in the referenced patents.

Figure 5:
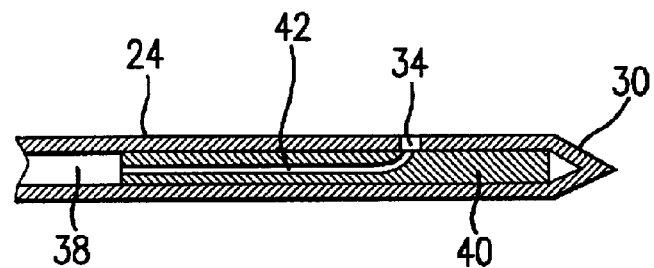
FIG. 5 is a simplified longitudinal cross-sectional view of the primary penetrating member.

The insert 40 illustrated in FIG. 5 has been simplified for purposes of illustration only by omitting the secondary penetrating member 26 and showing only one channel 42 corresponding to a single aperture 34. However, it is to be understood that a plurality of channels 42 may be provided to correspond to the number of secondary penetrating members 26 and the number of apertures 34 utilized.

Figure 6A:
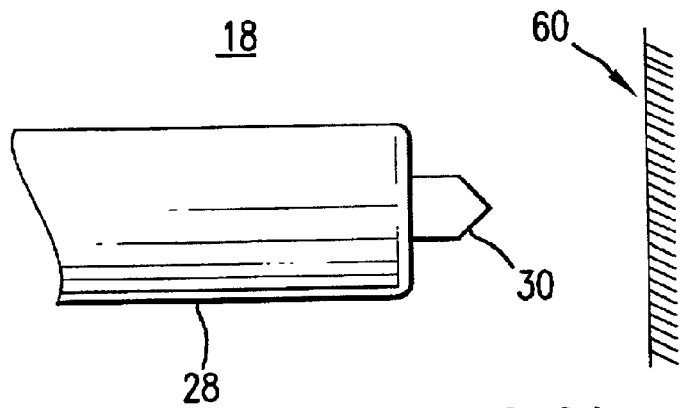
FIGS. 6A–6C illustrate a sequence of steps for using the system illustrated in FIG. 1A.
Figure 6B:
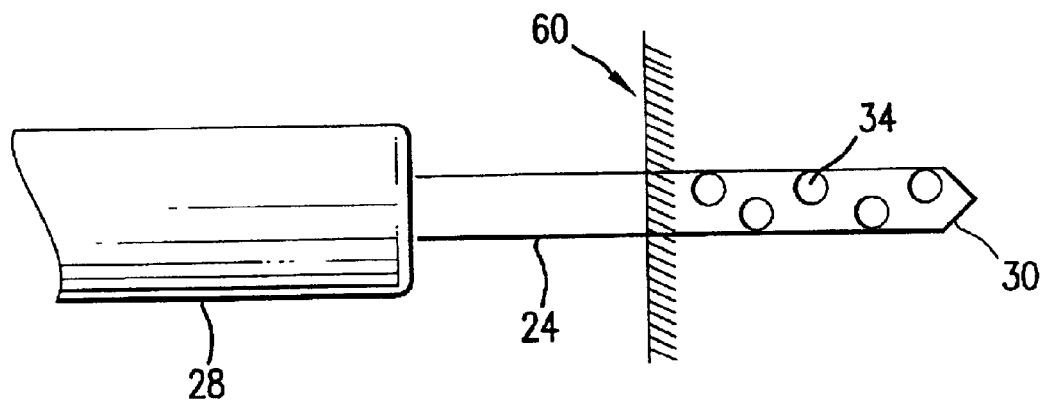
Figure 6C:
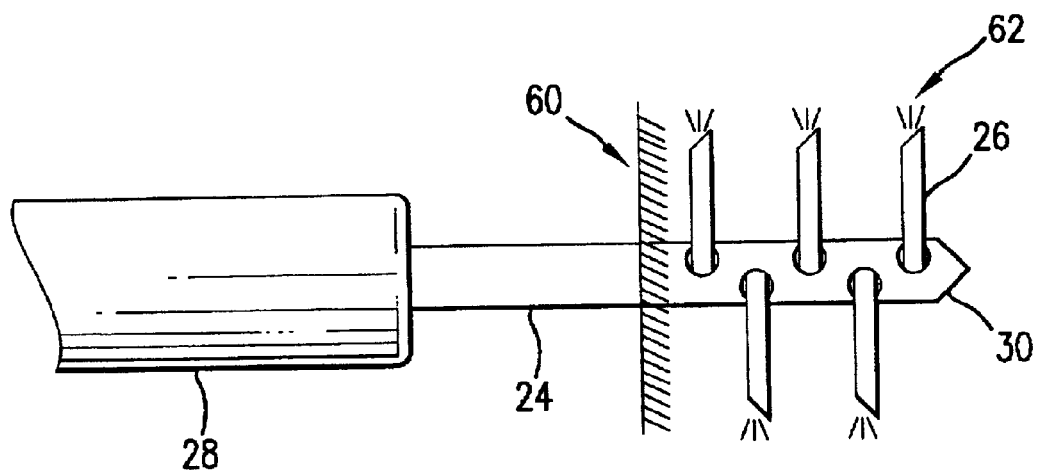

Refer now to FIGS. 6A–6C which illustrate operation of the catheter system 10. The heart tissue 60 (i.e., myocardium) may be accessed from the interior of the heart by, for example, navigating the catheter 12 through the vascular system into a chamber of the heart. Alternatively, the heart tissue 60 may be accessed from the exterior of the heart by, for example, transthoracic minimally invasive surgery in which the catheter 12 is navigated through the upper thoracic cavity adjacent the epicardium of the heart.

Regardless of the approach, the distal portion 18 of the catheter 12 is positioned adjacent the desired treatment site of the heart tissue 60 utilizing conventional visualization techniques such as x-ray, fluoroscopy, ultrasound, or endoscopic visualization. While positioning the catheter 12, the primary penetrating member 24 may be partially retracted in the outer sheath 28 such that only the distal end 30 of the primary penetrating member 24 is exposed, or fully retracted such that the entire primary penetrating member 24 is contained within the outer sheath 28.

With the distal portion 18 positioned adjacent the heart tissue 60 as shown in FIG. 6A, the primary penetrating member 24 is advanced into the heart tissue 60 until the distal end 30 of the primary penetrating member 24 reaches a sufficient depth to position the apertures 34 completely within the tissue 60 as shown in FIG. 6B. This position may be confirmed by injecting radiopaque contrast media or colored dye through the inner lumen 38 of the primary penetrating member 24 such that the contrast media or dye exits the apertures 34.

Once the primary penetrating member 24 is in position, the secondary penetrating members 26 may be actuated from the retracted position to the extended position as shown in FIG. 6C. Once in the extended position, fluid 62 may be infused from the pressurized fluid source 20 through the injection lumens of the secondary penetrating members 26 and into the heart tissue 60. The pressure applied by the pressurized fluid source 20 to deliver the fluid 62 into the heart tissue 60 may vary depending on the desired result. For example, a relatively low pressure of approximately 0.01 to 1 ATM may be utilized to deliver the fluid 62 into the heart tissue 60 thereby minimizing trauma to the tissue adjacent the injection site. Alternatively, a relatively high pressure of approximately 30 to 300 ATM may be utilized to increase the depth penetration of the fluid 62 into the heart tissue 60.

After the fluid 62 has been delivered via the injection lumens in the secondary penetrating members 26, the secondary penetrating members 26 may be retracted into the primary penetrating member 24. After retraction, the primary penetrating member 24 may be withdrawn from the heart tissue 60 and the entire catheter 12 may be removed from the patient.

As can be appreciated from the illustration of FIG. 6C, by injecting the fluid 62 in a direction different from the direction of penetration of the primary penetrating member 24, the fluid 62 will be retained within the heart tissue 60. Retention of the fluid 62 in the heart tissue 60 is primarily accomplished by injecting the fluid 62 into the heart tissue 60 in a direction different from the direction of penetration of the primary penetrating member 24. In addition to providing better retention of the fluid 62 within the heart tissue 60, this arrangement also allows for a greater volume of heart tissue 60 to be treated with a single primary penetration.

Thus, to accomplish this result, the secondary penetrating members 26 may be advanced into the heart tissue 60 at a different angle than the angle of the primary penetrating member 24. Preferably, the secondary penetrating members 26 are advanced into the heart tissue 60 in a direction generally lateral or at an angle from the direction of the primary penetrating member 24. However, the secondary penetrating members 26 may penetrate the heart tissue 60 at an angle of 5 to 90 degrees relative to the direction of the primary penetrating member 24 to accomplish essentially the same result. The angle may be determined in part by the angle of the axis of each aperture 34 or by the means for directing the secondary penetrating members 26 as discussed previously. Also preferably, the primary penetrating member 24 penetrates the heart tissue 60 in a direction generally orthogonal to the surface of the heart tissue 60 adjacent the injection site.

Figure 7A:
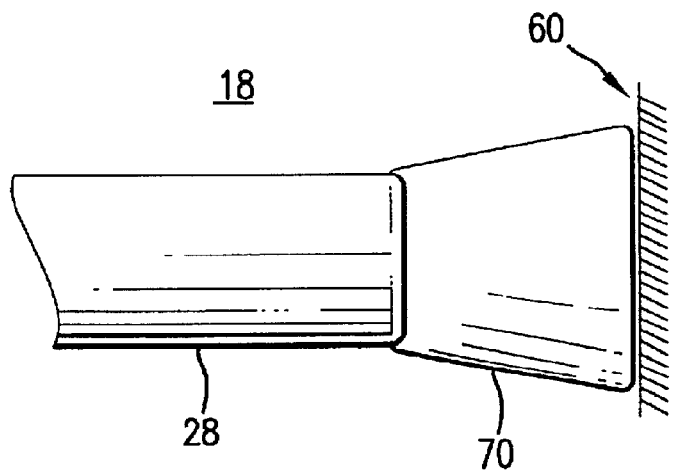
FIGS. 7A–7C illustrate a sequence of steps for using an alternative embodiment of the system illustrated in FIG. 1A, incorporating a stabilizing suction head.
Figure 7B:
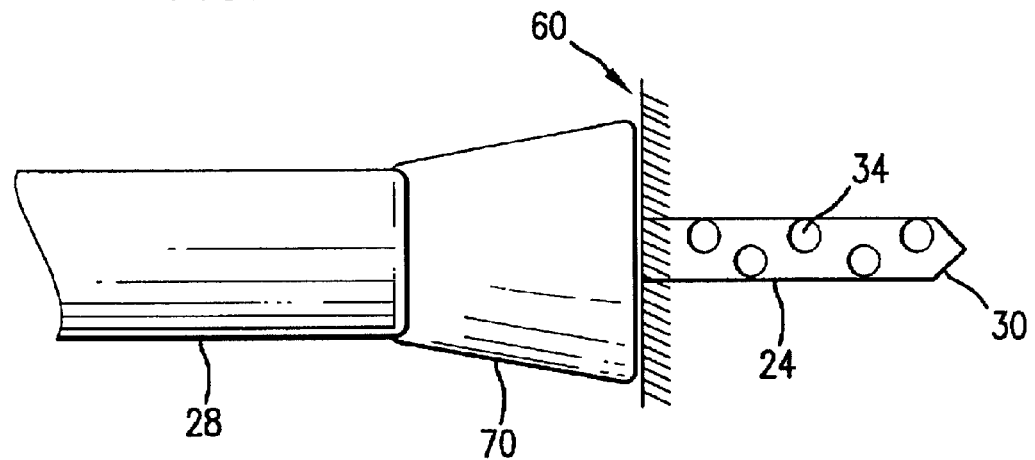
Figure 7C:
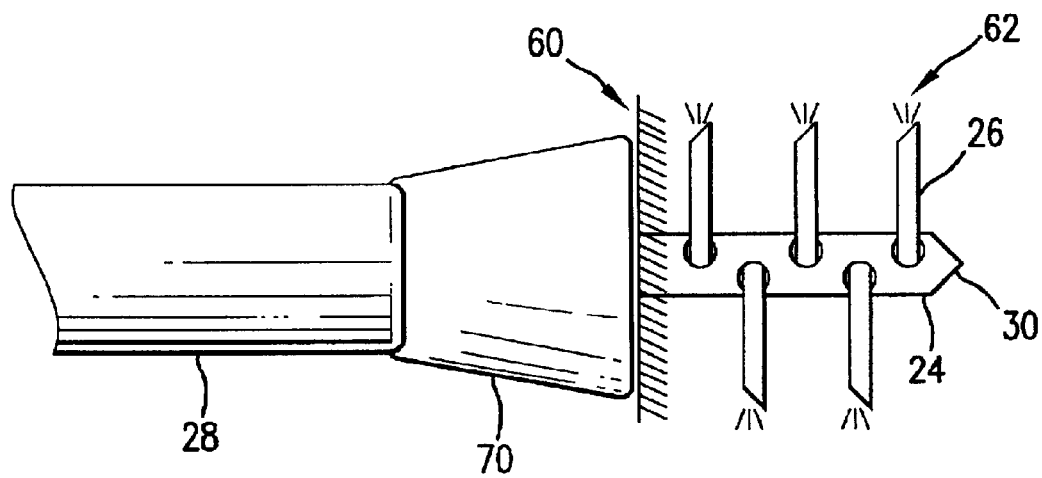

Refer now to FIGS. 7A–7C which illustrate operation of an alternative embodiment of the catheter system 10. In this particular embodiment, the distal portion of the catheter 12 incorporates a suction head 70 connected to the distal head of the outer sheath 28. The suction head 70 comprises a flexible tubular member having a generally conical shape. The suction head 70 has an interior which is in fluid communication with the inner lumen 36 of the outer sheath 28. As mentioned previously, the inner lumen 36 of the outer sheath 28 is in fluid communication with the vacuum source 22. By actuating the vacuum source 22, suction is applied to the suction head via the inner lumen 36 of the outer sheath 28.

The suction head is positioned adjacent the heart tissue 60 as illustrated in FIG. 7A. The suction head 70 grasps the surface of the heart tissue 60 thereby stabilizing the distal portion 18 of the catheter 12. This is particularly beneficial when treating tissue in a dynamic setting such as when the heart is beating. Absent a stabilizing means such as suction head 70, it maybe difficult to maintain the distal portion 18 in a relatively fixed position if the treatment site is not stationary. Those skilled in the art will recognize that other stabilizing means may be utilized such as removable screw anchors, miniature forceps, etc.

After suction is applied to the suction head 70 thereby stabilizing the distal portion 18 of the catheter 12, the primary penetrating member 24 is advanced into the heart tissue 60 as illustrated in FIG. 7B. Once the apertures 34 of the primary penetrating member 24 are completely embedded within the heart tissue 60, the secondary penetrating members 26 are actuated from their retracted position to their extended position as illustrated in FIG. 7C. Once extended, fluid 62 may be delivered into the heart tissue 60 via the injection lumens in the secondary penetrating members 26 as discussed previously.

After the fluid 62 has been delivered to the heart tissue 60, the secondary members 26 may be left in the tissue 60 for a period of time to allow the fluid 62 to be absorbed by the tissue 62. The amount of time required for the fluid 62 to be absorbed by the tissue 62 will vary depending on the volume of fluid delivered and the absorption characteristics of the tissue 62. The time period may be relatively short or prolonged, ranging, for example, from about 5 seconds to 2 minutes. Preferably, the time period ranges from about 5 seconds to about 30 seconds. When the secondary penetrating members 26 are subsequently withdrawn, leakage of the fluid 62 from the tissue 60 is further minimized or eliminated due to absorption thereof by the tissue 60.

After waiting the desired period of time, the secondary members 26 may be retracted into the primary penetrating member 24, and the primary penetrating member 24 may then be retracted into the outer sheath 28. After retracting the primary member 24, the suction applied by the suction head 70 is terminated to release the distal portion 18 of the catheter from the heart tissue 60. The entire catheter system 12 may then be removed from the patient.

In an embodiment of the present invention, a low volume (several microliters but less than 100 microliters by a single injection) of solution is delivered to the heart such that it may absorb the delivered solution within the time frame of the injection. In contrast to higher volume injections, the heart is more capable of absorbing these low volumes. The effect of the low volume injection is to minimize expulsion by the tissue. In order to deliver the entire dose of virus, it may be desirable or necessary to concentrate the injection (i.e., deliver the same number of viral particles or micrograms of protein, typically delivered in 100 μl, in a volume of 10 μl) or keep the concentration of virus the same as that typically used, but increase the number of injections from 10 (typical) to 20, 30, or more.

Each injectate may also be delivered in a prolonged manner such that the heart can absorb the solution as it is being injected (rate of delivery≦rate of tissue absorption). For instance, the injection can be delivered at a defined flow rate using a syringe pump. The time of injection will depend on the volume to be delivered. For example, low volumes (a few microliters) may be delivered in under a minute while higher volumes (10 to 100 μl or more) may be delivered over several minutes. In this instance, it may be beneficial to include a method which gently attaches the injection catheter to the wall of the heart, for instance suction or vacuum.

From the foregoing, it is apparent that the present invention provides a device and method for delivering and injecting fluid into heart tissue to improve the retention of the fluid in the heart tissue. This is accomplished by utilizing secondary penetrating members which penetrate heart tissue in a direction different from the direction of the primary penetrating member. Fluid may then be delivered via the secondary penetrating members such that the fluid leakage from the injection site is reduced and the fluid is distributed over a greater volume of tissue.

Although treatment of the heart is used as an example herein, the medical devices of the present invention are useful for treating any mammalian tissue or organ. Nonlimiting examples include tumors; organs including but not limited to the heart, lung, brain, liver, kidney, bladder, urethra and ureters, eye, intestines, stomach, pancreas, ovary, prostate; skeletal muscle; smooth muscle; breast, cartilage and bone.

The terms "therapeutic agents" and "drugs" are used interchangeably herein and include pharmaceutically active compounds, cells, nucleic acids with and without carrier vectors such as lipids, compacting agents (such as histones), virus, polymers, proteins, and the like, with or without targeting sequences.

Specific examples of therapeutic agents used in conjunction with the present invention include, for example, proteins, oligonucleotides, ribozymes, anti-sense genes, DNA compacting agents, gene/vector systems (i.e., anything that allows for the uptake and expression of nucleic acids), nucleic acids (including, for example, recombinant nucleic acids; naked DNA, cDNA, RNA; genomic DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application. Other pharmaceutically active materials include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof.

Examples of polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins useful in the present invention include, without limitation, angiogenic factors and other molecules competent to induce angiogenesis, including acidic and basic fibroblast growth factors, vascular endothelial growth factor, hif-1, epidermal growth factor, transforming growth factor α and β platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP- 12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

The present invention is also useful in delivering cells as the therapeutic agent. Cells can be of human origin (autologous or allogeneic) or from an animal source (xenogeneic), genetically engineered if desired to deliver proteins of interest at a delivery or transplant site. The delivery media is formulated as needed to maintain cell function and viability.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A catheter comprising:
   a shaft having a proximal end and a distal end and a wall defining at least one aperture, the distal end of the shaft including a primary penetrating member having a sharpened end and at least one secondary penetrating member having a sharpened end, wherein the primary penetrating member is adapted to penetrate tissue in a first direction, and wherein the at least one secondary penetrating member is retractable to a position within the primary penetrating member and penetrates the tissue in a second direction different from the first direction when extended from the primary penetrating member, the shaft further comprising an insert having a lumen extending in a longitudinal direction of the shaft and transitioning to a generally lateral direction adjacent the at least one aperture to direct the at least one secondary member through the at least one aperture.

2. The catheter of claim 1, wherein the tissue is selected from the group consisting of tumors, heart, lung, brain, liver, kidney, bladder, urethra, ureters, eye, intestines, stomach, pancreas, ovary, prostate, skeletal muscle, smooth muscle, breast, cartilage and bone.

3. The catheter of claim 1, wherein the at least one secondary penetrating member comprises microneedles.

4. The catheter of claim 1, wherein the second direction is generally perpendicular to the first direction.

5. The catheter of claim 1, wherein the second direction is at an angle of about 5 to about 90 degrees relative to the first direction.

6. A catheter system comprising:
   a pressurized fluid source including fluid therein, and
   a catheter having a proximal end and a distal end and a wall defining at least one aperture, wherein the proximal end of the catheter is connected to the pressurized fluid source, wherein the distal end of the catheter includes a primary penetrating member having a sharpened end and at least one secondary penetrating members having a sharpened end, wherein the primary penetrating member is adapted to penetrate tissue in a first direction, and wherein each of the at least one secondary penetrating members is retractable to a first position within the primary penetrating member and a second position extended from the primary penetrating member, with each of the least one secondary penetrating members having a lumen in fluid communication with the pressurized fluid source such that fluid may be delivered to the tissue via the secondary penetrating members, the shaft further comprising an insert having a lumen extending in a longitudinal direction of the shaft and transitioning to a generally lateral direction adjacent the at least one aperture to direct the at least one secondary member through the at least one aperture.

7. The catheter system of claim 6, wherein the secondary penetrating members penetrate the tissue in a second direction different from the first direction when extended from the primary penetrating member.

8. The catheter system of claim 6, wherein the second direction is generally perpendicular to the first direction.

9. The catheter system of claim 6, wherein the second direction is at an angle of about 5 to about 90 degrees relative to the first direction.

10. The catheter system of claim 6, wherein the tissue is selected from the group consisting of tumors, heart, lung, brain, liver, kidney, bladder, urethra, ureters, eye, intestines, stomach, pancreas, ovary, prostate, skeletal muscle, smooth muscle, breast, cartilage and bone.

11. The catheter system of claim 6, wherein the fluid comprises at least one therapeutic agent.

12. The catheter system of claim 6, wherein the at least one secondary penetrating member comprises microneedles.

* * * * *

UNITED STATES PATENT AND TRADEMARK OFFICE
CERTIFICATE OF CORRECTION

PATENT NO. : 6,969,371 B2
DATED : November 29, 2005
INVENTOR(S) : Palasis et al.

Page 1 of 1

It is certified that error appears in the above-identified patent and that said Letters Patent is hereby corrected as shown below:

Column 9,
Line 56, change "viral, liposomes" to -- viral liposomes --;

Column 10,
Line 9, change "nitorfurantoin" to -- nitrofurantoin --;
Line 11, change "lisidomine" to -- linsidomine --;
Line 17, change "Warafin" to -- Warfarin --;
Lines 20 and 22, change "promotors" to -- promoters --;
Line 30, change "endogeneus" to -- endogenous --.

Signed and Sealed this

Twenty-first Day of March, 2006

JON W. DUDAS
*Director of the United States Patent and Trademark Office*